US008705828B2

(12) United States Patent  (10) Patent No.: US 8,705,828 B2
Yang et al.  (45) Date of Patent: Apr. 22, 2014

(54) METHODS AND APPARATUS FOR SUPER RESOLUTION SCANNING FOR CBCT SYSTEM AND CONE-BEAM IMAGE RECONSTRUCTION

(75) Inventors: Dong Yang, Pittsford, NY (US); Nathan J. Packard, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 407 days.

(21) Appl. No.: 13/222,461

(22) Filed: Aug. 31, 2011

(65) Prior Publication Data

US 2013/0051519 A1  Feb. 28, 2013

(51) Int. Cl.
 *G06K 9/00* (2006.01)
 *A61B 6/00* (2006.01)
(52) U.S. Cl.
 USPC .............................. 382/131; 382/285; 378/16
(58) Field of Classification Search
 CPC ....................................................... A61B 6/27
 USPC ......... 382/100, 103, 118, 128–134, 154–155, 382/162, 168, 173, 181, 232, 254–263, 382/274–276, 285, 305, 312; 600/417; 378/21, 16, 154
 See application file for complete search history.

(56) References Cited

U.S. PATENT DOCUMENTS

| 5,270,926 | A | 12/1993 | Tam |
| 5,999,587 | A | 12/1999 | Ning et al. |
| 6,895,080 | B2 * | 5/2005 | Baba et al. ................. 378/154 |
| 8,009,890 | B2 * | 8/2011 | Nishide et al. ............. 382/131 |
| 8,194,937 | B2 * | 6/2012 | Chen .......................... 382/118 |
| 2006/0050842 | A1 * | 3/2006 | Wang et al. ................. 378/16 |
| 2013/0303884 | A1 * | 11/2013 | Kuntz et al. ................ 600/417 |

OTHER PUBLICATIONS

Jiang Liu et al., "Pseudo super-resolution for improved calcification characterization for Cone Beam Breast CT (CBBCT)", Medical Imaging 2010: Physics of Medical Imaging, Proc. of SPIE, vol. 7622, Doi: 10.1117/12.844353, 9 pases.*
L.A. Feldkamp et al., "Practical cone-beam algorithm", 1984 Optical Society of America, vol. 1, No. 6, Jun. 1984, pp. 612-619.
Jiang Liu et al., "Pseudo super-resolution for improved calcification characterization for Cone Beam Breast CT (CBBCT)", Medical Imaging 2010: Physics of Medical Imaging, Proc. of SPIE, vol. 7622, Doi: 10.1117/12.844353, 9 pages.

* cited by examiner

*Primary Examiner* — Seyed Azarian

(57) ABSTRACT

Embodiments of methods and/or apparatus for 3-D volume image reconstruction of a subject, executed at least in part on a computer for use with a digital radiographic apparatus can obtain image data for 2-D projection images over a range of scan angles. For each of the plurality of projection images, an enhanced projection image can be generated. In one embodiment, through the application of a resolution increasing interpolator, a prescribed CBCT routine scanning mode with pre-set binning can increase a spatial resolution, Nyquist frequency or MTF.

17 Claims, 9 Drawing Sheets

METHODS AND APPARATUS FOR SUPER RESOLUTION SCANNING FOR CBCT SYSTEM AND CONE-BEAM IMAGE RECONSTRUCTION

FIELD OF THE INVENTION

The invention relates generally to the field of digital radiography, diagnostic imaging and more particularly to Cone-Beam Computed Tomography (CBCT) imaging. More specifically, the application relates to methods and apparatus for improved resolution in projection data of CBCT image content.

BACKGROUND OF THE INVENTION

Three-dimensional (3-D) volume imaging has proved to be a valuable diagnostic tool that offers significant advantages over earlier two-dimensional (2-D) radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Conventional computed tomography CT scanners direct a fan-shaped X-ray beam through the patient or other subject and toward a one-dimensional detector, reconstructing a succession of single slices to obtain a volume or 3-D image. Cone-beam computed tomography or CBCT scanning makes it possible to improve image capture and processing speeds by directing a cone-beam source toward the subject and obtaining the image on a flat-panel X-ray detector. In cone-beam computed tomography scanning, a 3-D image is reconstructed from numerous individual scan projections, each taken at a different angle, whose image data is aligned and processed in order to generate and present data as a collection of volume pixels or voxels.

The processing of CBCT data for obtaining images requires some type of reconstruction algorithm. Various types of image reconstruction have been proposed, generally classified as (i) exact or approximate, or (ii) iterative or analytic. Exact cone-beam reconstruction algorithms, based on theoretical work of a number of researchers, require that the following sufficient condition be satisfied: "on every plane that intersects the imaged object there exists at least one cone-beam source". The widely used Grangeat algorithm, familiar to those skilled in CBCT image processing, is limited to circular scanning trajectory and spherical objects. Only recently, with generalization of the Grangeat formula, is exact reconstruction possible in spiral/helical trajectory with longitudinally truncated data.

Despite advances in exact methods (i, above), approximate methods (ii) continue to be more widely used. Chief among these CBCT reconstruction approaches and familiar to those skilled in the CT imaging arts are the Feldkamp/Davis/Kress (FDK) based algorithms.

Although 3-D images of diagnostic quality can be generated using CBCT systems and technology, however, a number of technical challenges remain.

Increased resolution in the digital image domain (e.g., 2D projection images) is desirable. There is a compelling need for improved methods for increased resolution techniques in the volume DR image reconstruction processing.

SUMMARY OF THE INVENTION

Accordingly, it is an aspect of this application to address in whole or in part, at least the foregoing and other deficiencies in the related art.

It is another aspect of this application to provide in whole or in part, at least the advantages described herein.

Another aspect of this application is to provide methods and/or systems that can address increased resolution in volume DR image reconstruction processing such as CBCT volume DR image reconstruction.

Another aspect of this application is to provide methods and/or systems capable of increased resolution in 2D projection images that can be used to increase the quality (e.g., MTF, resolution, contrast) in resultant volume DR image reconstruction such as CBCT volume DR image reconstruction.

Another aspect of this application is to provide improved resolution in image processing methods for CBCT images. Another aspect of this application is to provide higher resolution at decreased exposure times or increased image data frames per second (fps) in image processing methods for CBCT images. A related aspect is to maintain exposure levels while increasing resolution in the imaging chain, for example, prior to back projection and image reconstruction processing.

Another aspect of this application is that it can provide or use embodiments of systems and/or methods to provide increased resolution techniques or super-resolution techniques that can generate additional information from an image such as the high frequency components from a low resolution image. The additional information or high frequency components can be used to improve resultant digital images. Embodiments can use an interpolator such as a neural network interpolator trained on a higher resolution image to increase resolution of projection image data obtained at a prescribed binning mode. Embodiments can use a neural network interpolator trained on a different object to increase resolution of projection image data obtained at a prescribed binning mode.

These objects are given only by way of illustrative example, and such objects may be exemplary of one or more embodiments of the application. Other desirable objectives and advantages inherently achieved by the disclosed embodiments or combinations thereof may occur or become apparent to those skilled in the art. The invention is defined by the appended claims.

According to one embodiment of the invention, there is provided a method for digital radiographic 3D volume image reconstruction of a subject, executed at least in part on a computer, that can include obtaining image data at a first binning mode for a plurality of 2D projection images over a range of scan angles; generating, for each of the plurality of 2D projection images, an increased-spatial resolution projection image by: (i) determining an image representation of a different corresponding object at a second higher spatial resolution binning mode; (ii) obtaining an image data transformation for the first binning mode according to the image representation obtained at the second higher spatial resolution binning mode; and (iii) applying the image data transformation individually to the plurality of 2D projection images obtained at the first binning mode to generate the increased-spatial resolution plurality of 2D projection images; and storing the increased-spatial resolution plurality of 2D projection images in a computer-accessible memory.

According to one embodiment of the invention, there is provided a method for digital radiographic 3D volume image reconstruction of a subject, executed at least in part on a computer, that can include obtaining cone-beam computed tomography image data at a first binning mode for a plurality of 2D projection images over a range of scan angles; generating, for each of the plurality of 2D projection images, an increased-spatial resolution projection image by (i) providing an image data transformation for the first binning mode according to image data from a second higher spatial resolution binning mode; and (ii) applying the image data transformation individually to the plurality of 2D projection images obtained at the first binning mode to generate the increased-spatial resolution plurality of 2D projection images; and storing the increased-spatial resolution plurality of 2D projection images in a computer-accessible memory.

According to one embodiment of the invention, there is provided a digital radiography CBCT imaging system for digital radiographic 3D volume image reconstruction of a subject that can include a DR detector to obtain a plurality of CBCT 2D projection images over a range of scan angles at a first binning mode; a computational unit to generate, for each of the plurality of 2D projection images, an increased-spatial resolution projection image, the computational unit to select (i) an image data transformation for the first binning mode according to image data from a second higher spatial resolution binning mode, and (ii) apply the image data transformation individually to the plurality of 2D projection images obtained at the first binning mode to generate the increased-spatial resolution plurality of 2D projection images; and a processor to store the increased-spatial resolution plurality of 2D projection images in a computer-readable memory.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
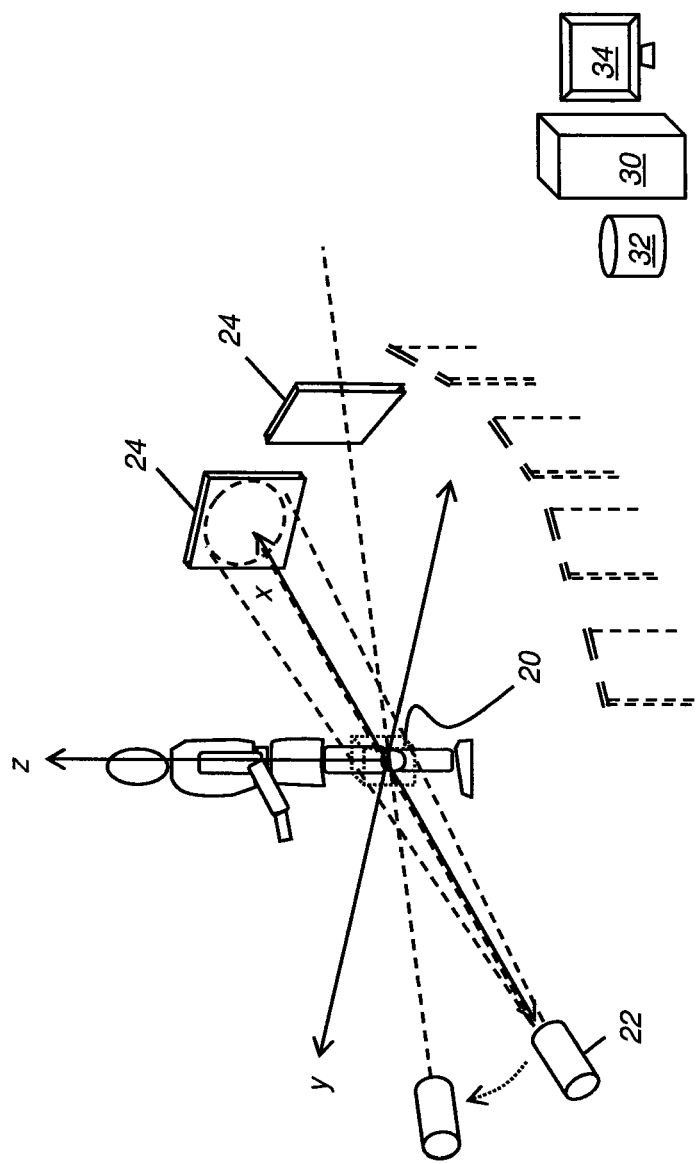
FIG. 1 is a schematic diagram showing components and architecture used for conventional CBCT scanning.

The following is a description of exemplary embodiments according to the application, reference being made to the drawings in which the same reference numerals identify the same elements of structure in each of the several figures, and similar descriptions concerning components and arrangement or interaction of components already described are omitted. Where they are used, the terms "first", "second", and so on, do not necessarily denote any ordinal or priority relation, but may simply be used to more clearly distinguish one element from another.

CBCT imaging apparatus and imaging algorithms used to obtain 3-D volume images using such systems are well known in the diagnostic imaging art and are, therefore, not described in detail in the present application. Some exemplary algorithms for forming 3-D volume images from the source 2-D images, projection images that are obtained in operation of the CBCT imaging apparatus can be found, for example, in Feldkamp L A, Davis L C and Kress J W, 1984, Practical cone-beam algorithm, J Opt Soc Am, A6, 612-619.

In typical applications, a computer or other type of dedicated logic processor for obtaining, processing, and storing image data is part of the CBCT system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the present application.

To understand exemplary methods and/or apparatus embodiments according to the present application and problems addressed by embodiments, it is instructive to review principles and terminology used for CBCT image capture and reconstruction. Referring to the perspective view of FIG. 1, there is shown, in schematic form and using exaggerated distances for clarity of description, the activity of an exemplary conventional CBCT imaging apparatus for obtaining the individual 2-D images that are used to form a 3-D volume image. A cone-beam radiation source 22 directs a cone of radiation toward a subject 20, such as a patient or other imaged subject. A sequence of images of subject 20 is obtained in rapid succession at varying angles about the subject over a range of scan angles, such as one image at each 1-degree angle increment in a 200-degree orbit. A DR detector 24 is moved to different imaging positions about subject 20 in concert with corresponding movement of radiation source 22. For example, such corresponding movement can have a prescribed 2D or 3D relationship. FIG. 1 shows a representative sampling of DR detector 24 positions to illustrate how these images are obtained relative to the position of subject 20. Once the needed 2-D projection images are captured in a prescribed sequence, a suitable imaging algorithm, such as FDK filtered back projection or other conventional technique, can be used for generating the 3-D volume image. Image acquisition and program execution are performed by a computer 30 or by a networked group of computers 30 that are in image data communication with DR detectors 24. Image processing and storage is performed using a computer-accessible memory in image data communication with DR detectors 24 such as computer-accessible memory 32. The 3-D volume image or exemplary 2-D image data can be presented on a display 34.

Figure 2:
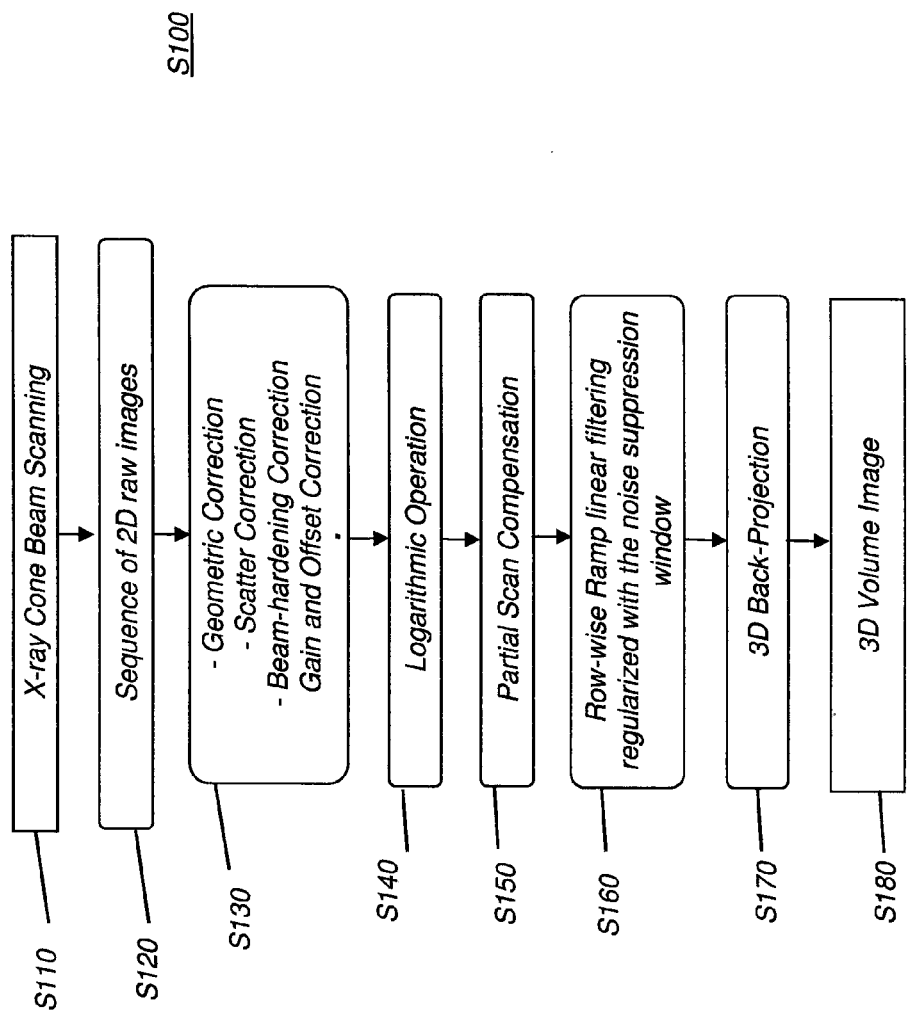
FIG. 2 is a logic flow diagram showing the sequence of processes used for conventional CBCT volume image reconstruction.

The logic flow diagram of FIG. 2 shows a conventional image processing sequence S100 for CBCT reconstruction using partial scans. A scanning step S110 directs cone beam exposure toward the subject, enabling collection of a sequence of 2-D raw data images for projection over a range of angles in an image data acquisition step S120. An image correction step S130 then performs standard processing of the projection images such as but not limited to geometric correction, scatter correction, gain and offset correction, and beam hardening correction. A logarithmic operation step S140 obtains the line integral data that is used for conventional reconstruction methods, such as the FDK method well-known to those skilled in the volume image reconstruction arts.

An optional partial scan compensation step S150 is then executed when it is necessary to correct for constrained scan data or image truncation and related problems that relate to positioning the detector about the imaged subject throughout the scan orbit. A ramp filtering step S160 follows, providing row-wise linear filtering that is regularized with the noise suppression window in conventional processing. A back projection step S170 is then executed and an image formation step S180 reconstructs the 3-D volume image using one or more of the non-truncation corrected images. FDK processing generally encompasses the procedures of steps S160 and S170. The reconstructed 3-D image can then be stored in a computer-accessible memory and displayed.

Conventional image processing sequence S100 of FIG. 2 has been proven and refined in numerous cases with both phantom and patient images.

It is desirable to increase resolution in the digital radiographic image domain preferably while maintaining or reducing radiographic exposure levels. Embodiments of systems and/or methods in accordance with the application provide increased resolution techniques or super-resolution techniques that can generate additional information from an image such as the high frequency components from the low resolution image. The additional information or high frequency components can be used to improve resultant digital images. For example, abnormal parts in digital radiographic images or DR medical images can be better characterized for diagnosis.

One related art method to obtaining super-resolved images is by using kernel functions, such as bilinear, bicubic, etc. However, techniques to obtain super resolution images using kernel functions have various disadvantages. One disadvantage with kernel super-resolution can be the blurring of sharp edges. Another disadvantage can be the introduction of blocking artifacts in diagonal edges or lines. Yet another disadvantage can be the inability to generate high frequency components or fine details.

Embodiments of systems and methods according to the application can use a CBCT imaging apparatus using a standard scanning mode with a first binning size to achieve increased spatial resolution such as a spatial resolution between the first binning size and a second higher resolution binning size under similar or the same operational/exposure settings. Embodiments of systems and methods according to the application can use a CBCT imaging apparatus using a standard scanning mode with 2 by 2 binning (e.g., first binning size) and super-resolution techniques to achieve increased spatial resolution such as a spatial resolution between 2 by 2 binning and 1 by 1 binning (e.g., second binning size) while maintaining a clinically acceptable signal to noise ratio (SNR), similar or the same X-ray exposure level and a similar or the same scanning time as the standard scanning mode with 2 by 2 binning. Thus, embodiments according to the application can better characterize structures (e.g., small structures) of the bone, improve characteristics or increase resolution of radiographic images provided. In one embodiment, CBCT imaging apparatus and/or methods maintain spatial resolution using reduced X-ray exposure level and increased resolution techniques with a standard scanning size binning mode.

Figure 3:
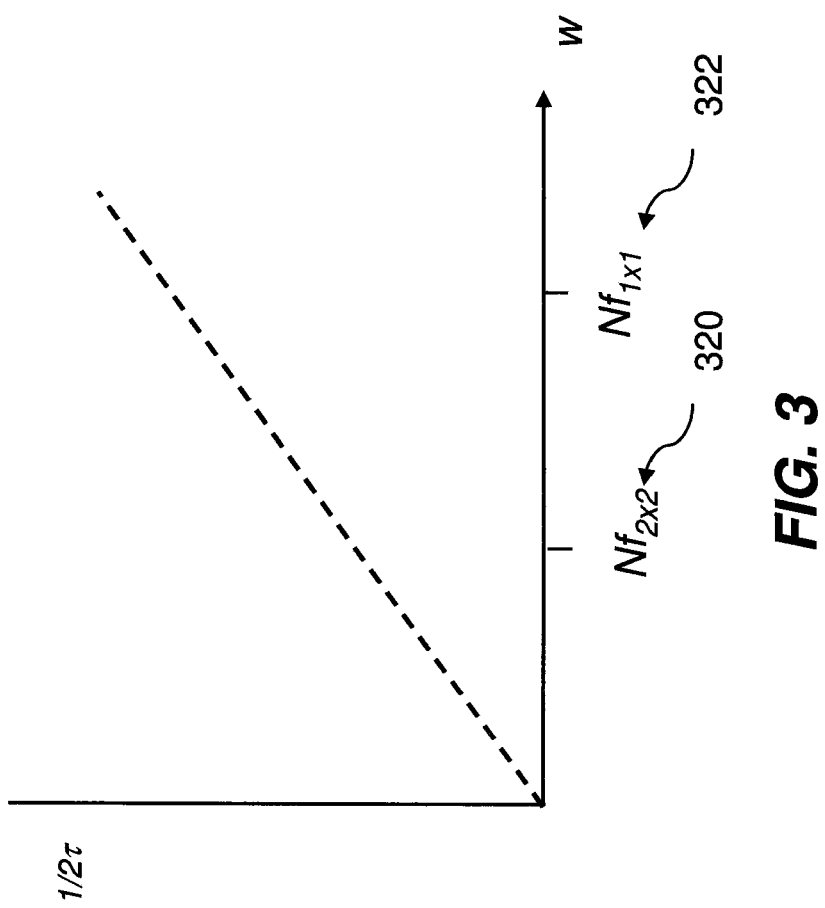
FIG. 3 is a graph that shows exemplary Nyquist frequencies for relative binning modes under similar operational conditions.

CBCT imaging systems can be equipped with a flat panel detector (e.g., rectangular or square DR detectors) in different two dimensional (2D) sizes and the flat panel detector (FPD) can have several available standard scanning or binning modes such as 1 by 1 binning, 2 by 2 binning, 2 by 1 binning, 1 by 2 binning, 4 by 4 binning or the like. In general, a highest spatial resolution can be achieved by binning using the original detector pixel pitch. For example, 1 by 1 binning can use the original detector pixel pitch and can then result in the largest Nyquist frequency value (e.g., highest spatial resolution). Further the highest spatial resolution (in this example 1 by 1 binning) generates the most data, which can be extremely large amounts of data. An exemplary CBCT scan can result in 300, 500, 1000 images or more from the FPD. In this case, 2 by 2 binning can theoretically have half of the Nyquist frequency value (e.g., half the spatial resolution) relative to the 1 by 1 binning. FIG. 3 is a diagram that illustrates respective Nyquist frequencies for exemplary binning modes in the frequency domain. As shown in FIG. 3, Nyquist frequency 320 $Nf_{2\times2}$ for 2 by 2 binning is about half the Nyquist frequency 322 $Nf_{1\times1}$ for 1 by 1 binning.

Considering frame readout rate is constant for a given FPD, the frame readout rate can be one factor to determine how long the CBCT imaging system or scanner will take to finish a complete scan of an object (e.g., one complete orbit of a gantry). A readout rate (e.g., frames per second) of the CBCT imaging system detector will be higher for a higher binning mode. Exemplary readout rate for CBCT imaging apparatus can be 10 fps for a 1 by 1 binning mode, 30 fps for a 2 by 2 binning mode, or 60 fps for a 4 by 4 binning mode.

In addition, the longer the time for CBCT scanning, the less immune to the motion artifacts are the reconstructed images.

Further, as pixel size decreases (e.g., FPD pixel size), independent of other factors, the radiation level must increase to maintain a given SNR. Accordingly, higher X-ray exposure levels are needed to achieve the same SNR when using 1 by 1 binning as compared to 2 by 2 binning. Thus, higher binning values such as 2 by 2 binning can be selected despite losing the spatial resolution. Currently, 2 by 2 binning can be considered one standard scanning mode for related art CBCT imaging systems.

Embodiments of methods and/or CBCT imaging systems according to the application can use resolution increasing methods or an up-scaling interpolator apparatus/unit to increase accuracy, reduce artifacts and/or generate new image information or additional fine details, etc. According to embodiments of the application, when a low resolution image (L) is present that is derived from a corresponding true high resolution image (H), and by using a scaling function $f(L,\alpha)$ with parameter $\alpha$, an up-scaled image $I=f(L,\alpha)$ can be obtained. The distance between the up-scaled image I and the true high resolution image H can be measured by some exemplary metric E(I,H), which can be called an error function. Then, the solution for finding a prescribed or an optimal set of parameters $\alpha$ can be addressed by an interpolator apparatus such as a neural network.

Embodiments of methods and/or CBCT imaging systems according to the application can use a computational unit, interpolator, Neural Network (NN) approximation methods or a NN interpolator to increase accuracy, reduce artifacts and/or generate higher image resolution or additional fine details, etc. Exemplary embodiments can use feed-forward neural networks (FFNN) as the interpolator apparatus because FFNN provide highly flexible models, however, embodiments are not intended to be limited to NN or FFNN.

Embodiments of methods and CBCT imaging systems according to the application can use super-resolution methods based on a single low resolution image.

Figure 4:
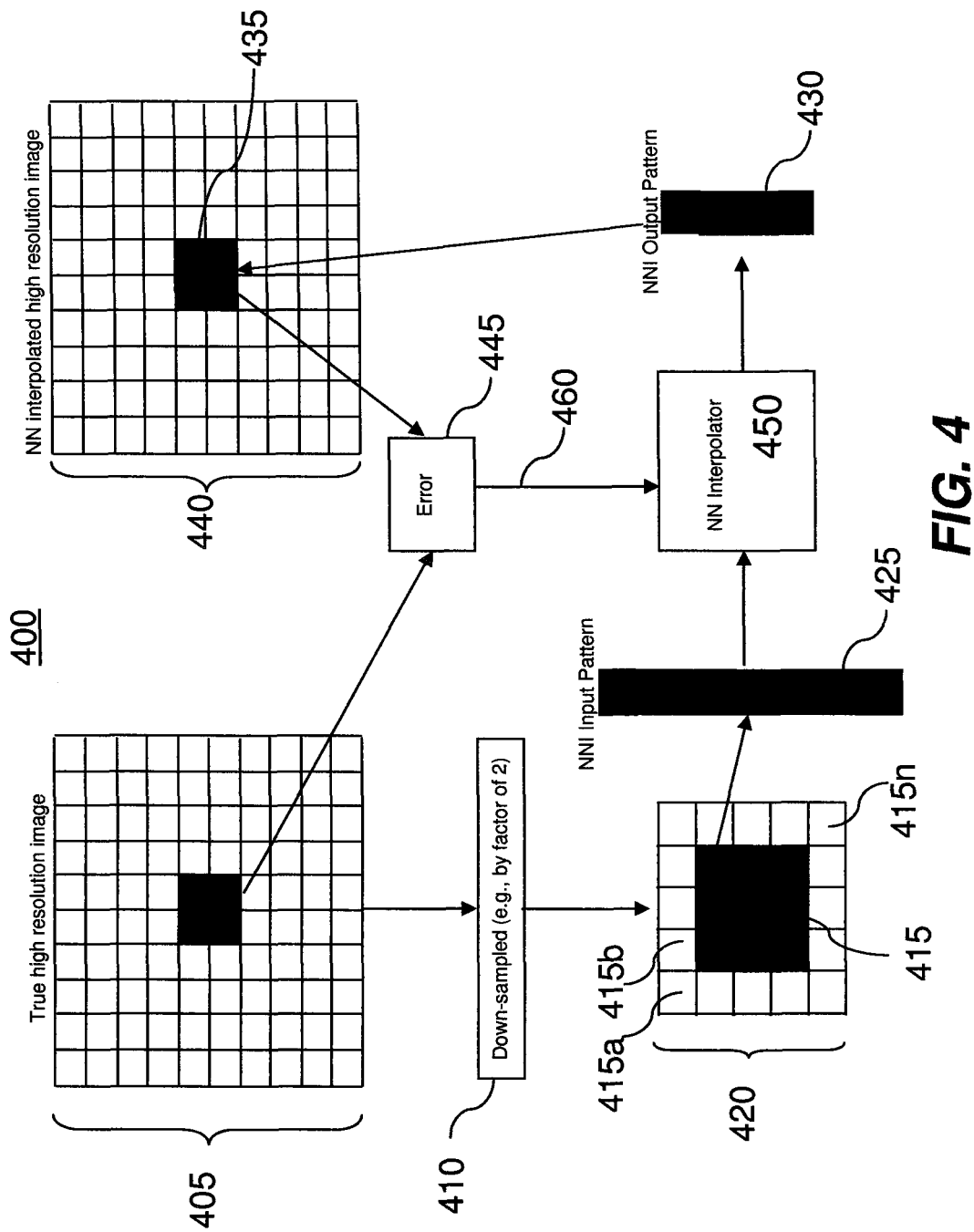
FIG. 4 is a diagram that shows an architecture of an exemplary neural net (NN) interpolator that can be used in embodiments of CBCT imaging systems (e.g., trained and/or operationally) according to the application.

An architecture of an exemplary neural net (NN)-based training system that can be used in embodiments of CBCT imaging systems according to the application is illustrated in FIG. 4. As shown in FIG. 4, during training operations an exemplary CBCT imaging system 400 can train a NN interpolator 450 for later use with imaging operations of a CBCT imaging system. For example, the NN interpolator 450 can be trained and later used by the same CBCT imaging system. Alternatively, the NN interpolator 450 can be trained and later used by the same type or model CBCT imaging system. Alternatively, the NN interpolator 450 can be trained and later used by a CBCT imaging system using the same x-ray source. Alternatively, the NN interpolator 450 can be trained and later used by a CBCT imaging system using the same examination settings (e.g., exposure, kVp settings and/or filtration settings (e.g., Al, Cu, specific thickness)). During such later imaging operations in the CBCT imaging system, the NN interpolator 450 can increase a modulation transfer function (MTF), increase a Nyquist frequency and/or increase spatial resolution of a standard operational scanning mode (e.g., 2 by 2 binning mode or a mode other than the highest spatial resolution mode) of the CBCT imaging system.

As shown in FIG. 4, a true high resolution image 405 can be obtained. As used herein, a true high resolution image can be defined as an image obtained at a higher spatial resolution and/or exposure settings above the corresponding subsequent super-resolution imaging operations. For example, a true high resolution image 405 can be a cadaver limb, cadaver knee, test object, subject, etc. imaged by the CBCT imaging system 400 at a high or maximum kVp and/or mAs settings with the detector mode at the highest spatial frequency or 1 by 1 binning mode. A single 2D image can be used for the true high resolution image 405 because the NN interpolator 450 can be a mechanism to increase spatial resolution or achieve a higher spatial frequency and can be angular independent. Thus, a single 2D true high resolution image 405 can be used for a single scan (e.g., 200 degrees, 240 degrees, 360 degrees) of the CBCT imaging system. Alternatively, a plurality of true high resolution images 405 can be used with a single scan of the CBCT imaging system. For example, 2, 5, 20, 50, 100 or more true high resolution images 405 can be used for a single scan of the CBCT imaging system. Preferably, the true high resolution image 405 is normalized to improve the efficiency of or simplify computational operations of the NN interpolator 450.

A true high resolution image can be generated and used for multiple lower resolution binning modes.

After the true high resolution image 405 is obtained, the true high resolution image 405 is down-sampled 410 (e.g., from the higher spatial resolution binning mode) to a first binning mode or lower spatial resolution binning mode. For down-sampling of the true high resolution image 405, various methods can be used, such as decimation, pixel averaging, median filtering, etc. In one exemplary embodiment of a CBCT imaging system, pixel averaging can be used in a down-sampling 410 unit to consistently follow the FPD physical operation and generate low resolution image 420. As shown in FIG. 4, the down sampling 410 can use a factor of 2 and can use pixel averaging to determine a single pixel value 415 (e.g., 415a, 415b, ..., 415n) of the low resolution image 420 that results from down sampling multiple pixel values of the true high resolution image 405.

During training operations, the system 400 can process a low resolution image 420 one pixel at a time. A neighborhood (e.g., 415a, ..., 415n) of a current pixel (e.g., 415) can be transformed into a fixed length vector (e.g., length 8), which can be the input 425 to the NN interpolator 450. As shown in FIG. 4, eight surrounding pixels of the pixel 415 can be used as the neighborhood of the pixel 415 being the current pixel. In one embodiment, the neighborhood of a current pixels can be a subset of the surrounding pixels (415a, ..., 415n). An output 430 of NN interpolator 450 can be a fixed length vector (e.g., length 4 of real numbers) that can be transformed into a plurality of high resolution pixels 435 in a modified high resolution output image or NN interpolated high resolution image 440 that correspond to the single pixel 415 in the low resolution image 420. Preferably, the output image 440 is the same resolution of the true high resolution image 405. When the true high resolution image 405 values are normalized, inputs to the NN interpolator 450 are normalized (e.g., from 0 to 1).

After each pixel in the low resolution image 420 is processed by the NN interpolator 450, an error 445 can be computed between the output image 440 and the true high resolution image 405, and a representation 460 of the error 445 such as the derivative can be back-propagated through the NN 450 to iteratively improve and refine the NN interpolator 450 approximation of the interpolation function (e.g., the mechanism to represent the line integral in the projection domain). In one embodiment, a global error can be determined for the error 445 and reduced or minimized during training operations of the NN interpolator 450. Completion of the NN interpolator 450 training can be variously defined, for example, when the error 445 is below a first threshold or a difference between subsequent iteration for the error 445 is below a second threshold, and then the NN 450 training can be terminated. Alternatively, a prescribed number of iterations can be used to train the NN interpolator 445 for the true high resolution image 405.

In one embodiment, each of a plurality of individual views or true high resolution images 405 can be used to train the NN interpolator 450 within a complete scan of the CBCT imaging system. For example, the NN interpolator 450 can be trained using a true high resolution image 405 for each 10 degrees of an exemplary CBCT imaging system scan. An exemplary CBCT imaging system scan can result in a prescribed number of raw 2D images, and alternatively the NN interpolator 450 can be trained every preset number of the prescribed raw 2D images. When trained with a plurality of true high resolution images 405, a single NN interpolation (e.g., set of weights in the NN) is preferably the result. Further, the CBCT imaging system can use a complete 360 degree scan of a subject or a partial 200-240 degree scan of the subject. In addition, the CBCT imaging system 400 can scan a weight bearing limb or extremity as the object.

Training of the NN interpolator 450 can be done on an object different than a subject being scanned during operational use of the NN interpolator 450 in normal imaging operations of the CBCT imaging system 400. In one embodiment, the training can be done on a corresponding feature (e.g., knee, elbow, foot, hand, wrist, dental arch) of a cadaver. Further, in another embodiment, the training can be done on a corresponding range of feature sizes or corresponding cadavers (e.g., male, adult, female, child, infant). Alternatively, training be done using a test object.

Figure 5:
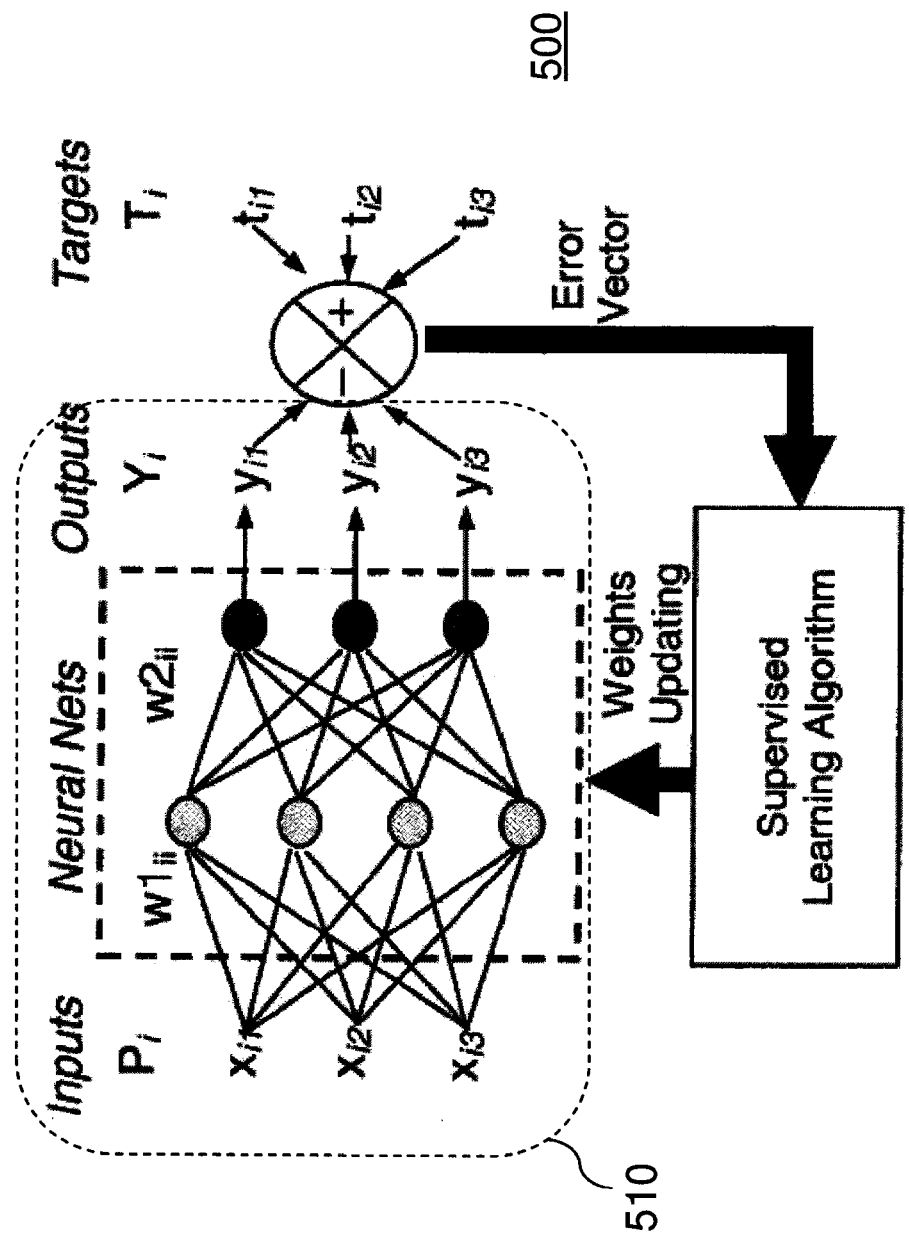
FIG. 5 is a diagram that shows a topological flow chart of exemplary artificial neural networks that can be used in embodiments according to the application.

FIG. 5 is a diagram that shows a topological flow diagram of exemplary artificial neural networks that can be used in embodiments according to the application. Thus, an exemplary NN 510 shown in FIG. 5 can be used for the NN interpolator 450, although embodiments are not intended to be limited thereby. An artificial neural network is a system based on the operation of biological neural networks, in other words, is an emulation of biological neural systems. A NN basically includes an input layer, hidden layers, an output layer and outputs as shown in FIG. 5.

A basic NN topological description follows. An input is presented to a neural network system 500 shown in FIG. 5 and a corresponding desired or target response is set at the output (when this is the case the training is called supervised). An error is composed from the difference between the desired (e.g., target) response and the NN output. Mathematically, the relationship between the inputs and outputs can be described as:

$$y_{ij} = \tanh\left(\sum_{j=1}^{4} w2_{ij}Z_j\right), \text{ where } Z_i = \tanh\left(\sum_{j=1}^{3} w1_{ij}X_{ij}\right)$$

In the expression above, tank is called an activation function that acts as a squashing function, such that the output of a neuron in a neural network is between certain values (e.g., usually between 0 and 1 or between −1 and 1). The bold black thick arrow indicates that the above NN system 500 is feed-forward back-propagated network. The error information is fed back in the NN system 500 during a training process and adaptively adjusts the NN 510 parameters (e.g., weights connecting the inputs to the hidden node and hidden nodes to the output nodes) in a systematic fashion (e.g., the learning rule). The process is repeated until the NN 510 or the NN system 500 performance is acceptable. After the training phase, the artificial neural network parameters are fixed and the NN 510 can be deployed to solve the problem at hand.

Figure 6:
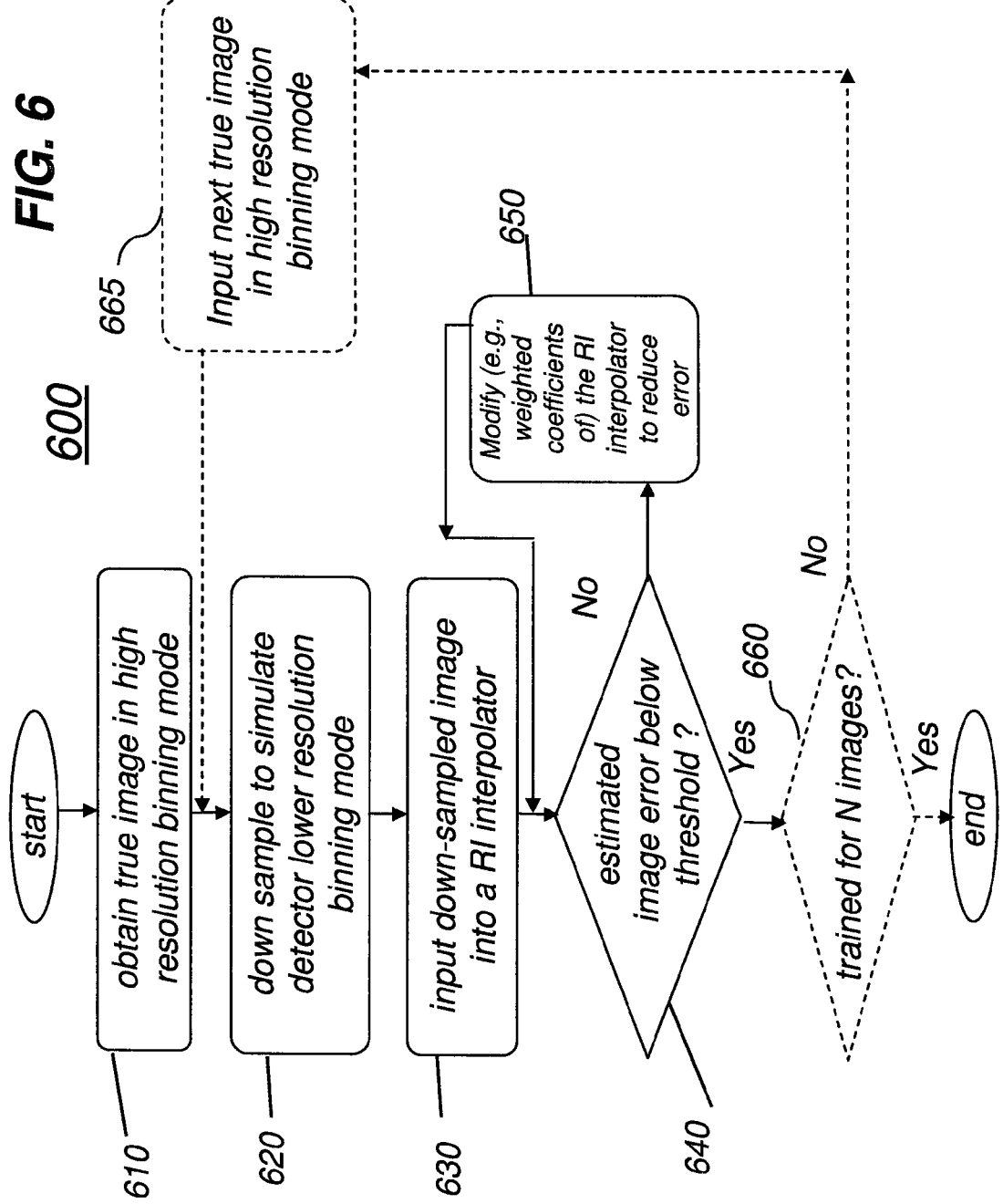
FIG. 6 is a flow chart that shows an exemplary method for using super-resolution modes in digital radiography systems according to embodiments of the application.

FIG. 6 is a flowchart of an exemplary method embodiment according to the application. As shown in FIG. 6, one method embodiment 600 of a super resolution imaging procedure for a CBCT imaging system according to the application can use the mechanism of a resolution increasing interpolator.

As shown in FIG. 6, after a process starts, a "true" image can be obtained (operation block 610). For example, a cadaveric knee can be exposed at a fixed view angle using highest exposure level a CBCT imaging system (e.g., system 100) can allow with a detector acquisition mode set at a prescribed resolution binning mode or a highest resolution (e.g., high resolution binning mode or 1 by 1 binning mode).

Then, the true high resolution image can be down sampled by a prescribed factor through an exemplary technique, for example 2 by 2 pixel averaging, which can result in a lower resolution image (operation block 620) that can correspond to a lower resolution binning mode (e.g., 2 by 2 binning mode) of a CBCT imaging system.

The down sampled image can be input (e.g., pixel by pixel) into a resolution increasing interpolator to output an estimated image (operation block 630). A target of the resolution increasing interpolator can be the true high resolution image generated in operation block 610.

Then, the resolution increasing interpolator can be trained (operation blocks 640, 650). For example, an output of the resolution increasing interpolator or the estimated image can be compared with the target and a currently calculated error therebetween can be input, fed back or back-propagated into the resolution increasing interpolator during training to refine or recalculate a modified output estimated image (operation block 640, no).

Training can be terminated once the error gets below a prescribed threshold (operation block 640, yes). The threshold can be a global error measurement for the entire estimated image or a localized error measurement for a portion or portions of the estimated image.

In one embodiment, a training process can end after training for a single image (operation block 640, yes). Alternatively, the resolution increasing interpolator can be trained for a plurality of true high resolution images as shown in dashed operation blocks 660, 665

According to exemplary embodiments, a trained resolution increasing interpolator from FIG. 6 can be applied to any projection images acquired through the lower resolution binning mode (e.g., 2 by 2 binning) of the DR detector using a CBCT system and that application can result in increase resolution of the resulting image or a super-resolution second binning mode. Thus, through the application of the trained resolution increasing interpolator, a current CBCT imaging system using a standard scanning mode with 2 by 2 binning can achieve the spatial resolution between 2 by 2 binning and 1 by 1 binning while one or more of a similar or clinically acceptable SNR, same X-ray exposure level or scanning time as the standard 2 by 2 binning can be maintained. Super-resolution binning modes can result in 2-D projection image data with a resolution increased relative to the 2-D projection image data from the corresponding standard binning mode, for example, to better characterize the tiny structures of the bone or allow the use of lower dose x-ray settings. In one embodiment, the NN interpolator 450, 950 can be used for the resolution increasing interpolator of FIG. 6.

Figure 7:
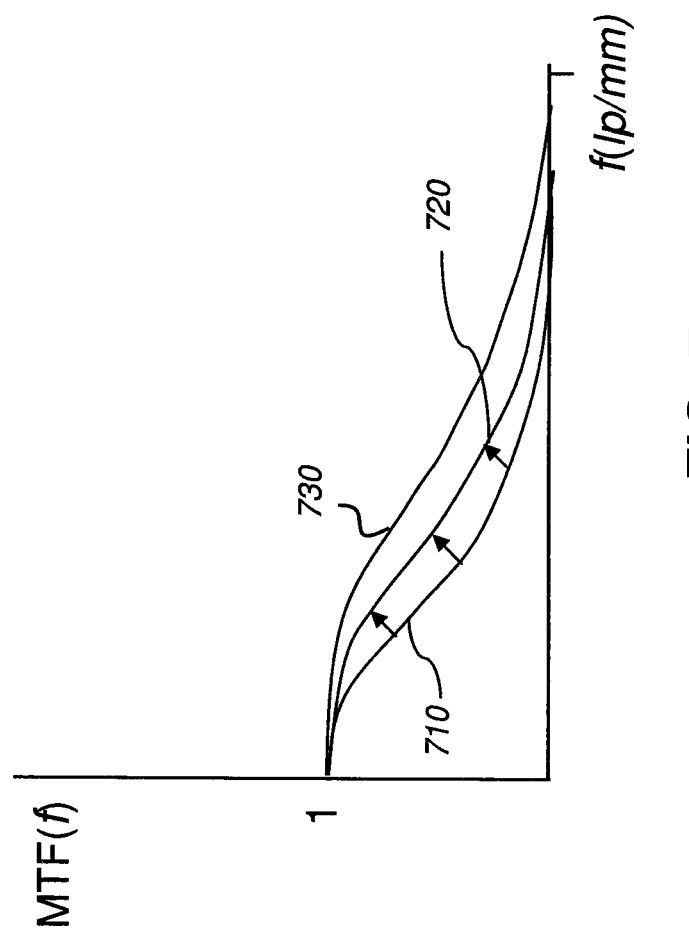
FIG. 7 is a graph that shows an increase in modulation transfer function (MTF) for exemplary embodiments of a super-resolution binning mode according to the application.

FIG. 7 is a diagram that illustrates an exemplary increase in MTF using system/method embodiments described herein. As shown in FIG. 7, an MTF 720 of a super resolution 2 by 2 binning mode is above and between an MTF 710 of a standard 2 by 2 binning mode, and a MTF 730 of a standard 1 by 1 binning mode.

Exemplary embodiments described herein take a novel approach to super resolution procedures by processing the projection data prior to reconstruction processing for 3D volume image reconstruction. An object is not uniformly sampled during a 3D rotational scanning (e.g., CBCT scanning) because the response of the detector to the sampled object is view dependent (e.g., in one view the response of the detector to a prescribed of the object structure (e.g., a tiny structure of bone) is small and in another view the response of the detector to the same structure can be big/larger/different). Embodiments according to the application can be one approach to use additional information (e.g., high frequency) in the plurality of 2D images to increase the resolution of the projection data that can then be used in volume image reconstruction.

Figure 8:
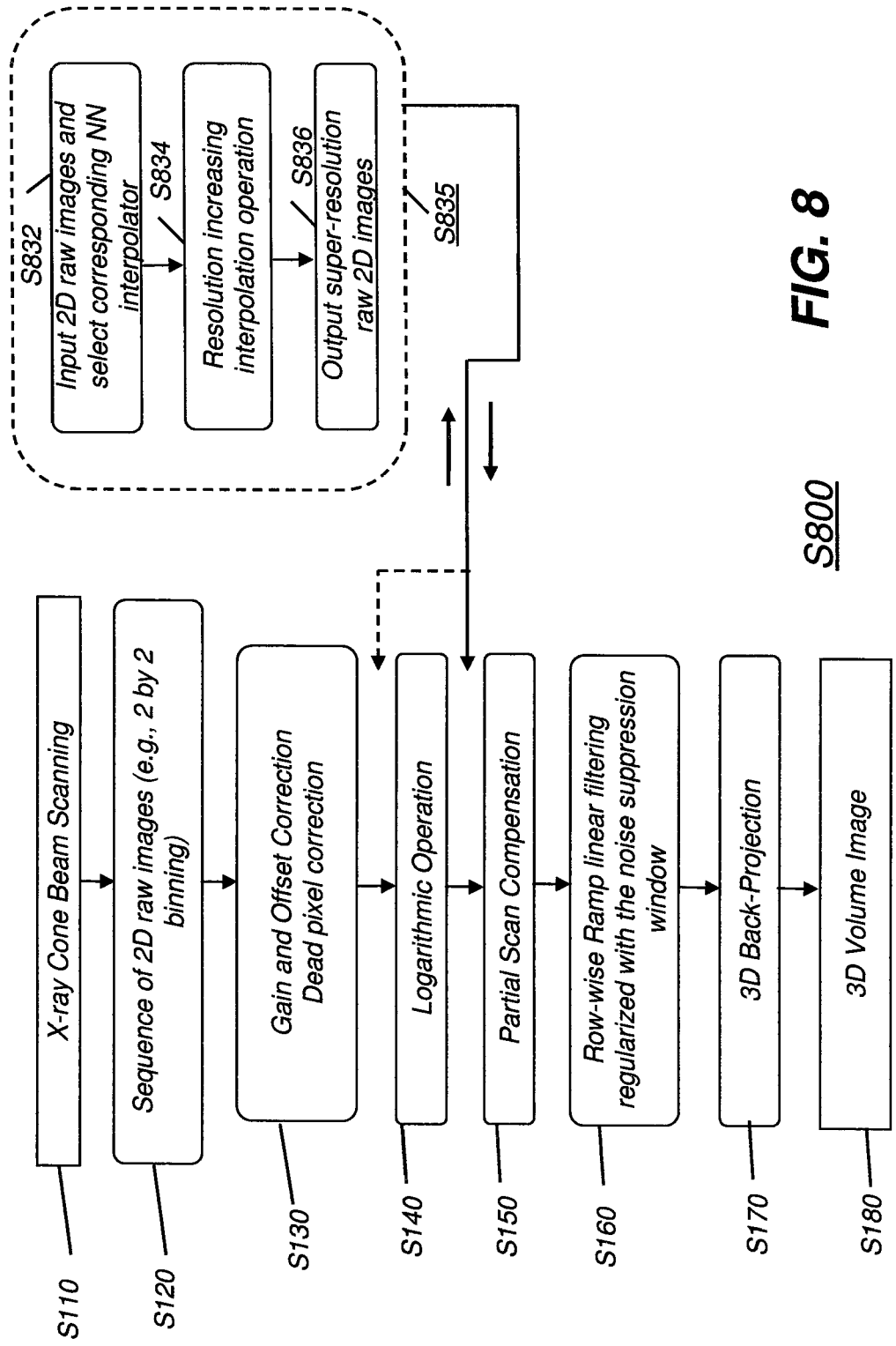
FIG. 8 is a logic flow diagram showing a sequence of processes used for 3-D volume image processing according to one embodiment of the application.

Referring to the logic flow diagram of FIG. 8, there is shown an image processing sequence S800 according to an embodiment of the application. Steps S110, S120, S130, S140, S150, S160, in this sequence are the same steps described earlier for the conventional sequence of FIG. 2. In this exemplary sequence, a super resolution process S835, indicated in dashed outline in FIG. 8, follows image correction step S130 or the logarithmic operation step S140 and can input raw 2D image data and output transformed raw 2D image data comprising additional information, output transformed raw 2D image data having a higher spatial resolution, and/or output transformed raw 2D image data including an increased Nyquist frequency.

As shown in FIG. 8, when a super resolution mode is selected for a standard binning mode, a NN interpolator for the corresponding examination (e.g., body part, exposure levels, etc.) is selected in step S832. Then, the raw 2D image data from the FPD with the selected standard binning mode can be passed through the selected NN interpolator (e.g., trained on the corresponding object) to determine transformed raw 2D image data having a higher spatial resolution (e.g., super-resolution raw 2D image data) in step 834. Then, the transformed raw 2D image data can be output for remaining volume image reconstruction processing in step 836.

Figure 9:
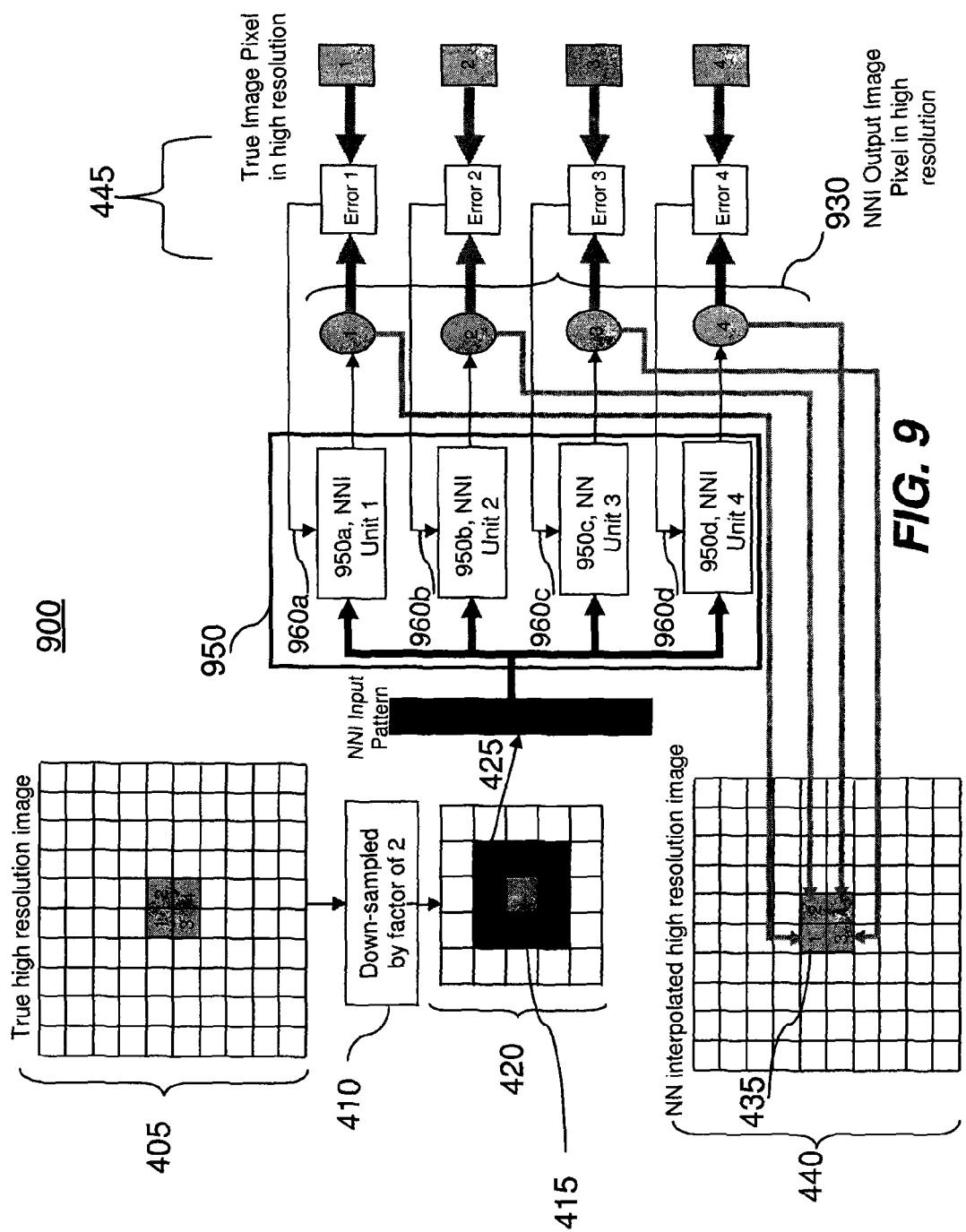
FIG. 9 is a diagram that shows another architecture of an exemplary neural net (NN) interpolator that can be used in embodiments of CBCT imaging systems (e.g., trained and/or operationally) according to the application.

An architecture of an exemplary NN-based training system that can be used in embodiments of CBCT imaging systems/methods according to the application is illustrated in FIG. 9. As shown in FIG. 9, an exemplary CBCT imaging system 900 can include a NN interpolator 950 that can use a plurality of NN interpolation units (e.g., 950a, 950b, ..., 950n).

During training operations, the system 900 can process a low resolution image 420 one pixel at a time. A neighborhood (e.g., 415a, ..., 415n) of a current pixel (e.g., 415) can be transformed into a fixed length vector (e.g., length 8), which can be the input 425 to the NN interpolator 950, and an output 930 of the NN interpolator 950 can be a fixed length vector (e.g., length 4 of real numbers) that can be transformed into a plurality of high resolution pixels 435 in the NN interpolated high resolution image 440 that correspond to the single pixel 415 in the low resolution image 420. The input 425 can be processed by each of the plurality of NN interpolation units 950a, 950b, 950c, 950d and an output of each can be a fixed length vector (e.g., length 1 of real numbers) that can be transformed into the plurality of high resolution pixels 435.

After each pixel in the low resolution image 420 is processed by the plurality of NN interpolation units 950a, 950b, 950c, 950d, an error 945a, 945b, 945c, 945d can be respectively computed between the output image 440 and the true high resolution image 405, and a representation 960a, 960b, 960c, 960d of the error 445 such as the derivative can be respectively back-propagated through each of the plurality of NN interpolation units 950a, 950b, 950c, 950d to iteratively improve and refine the NN interpolator 950 approximation of the interpolation function (e.g., the mechanism to represent the line integral in the projection domain).

Accordingly, in one embodiment, a plurality of NN interpolators can be used to estimate corresponding four high resolution pixel intensities (rather than a single NN interpolator), which can make exemplary super resolution techniques applied to CBCT imaging method/system embodiments described herein more robust and/or more accurate. In one embodiment, mechanisms for interpolation (e.g., NN interpolator 450, 950) can be the same whether only one NN interpolator or multiple NN interpolators are used.

In another exemplary embodiment according to the application, increased resolution can be accomplished between projection images resulting in additional projection images that can be used during reconstruction. For example, an interpolator such as a neural network (NN) interpolator can be trained on a set of N*2 projection images to increase the number of projection images of an acquisition of N projection images to N*2 projection images. These additional projection images can contribute to the overall image quality of the 3D reconstructed image.

In this embodiment, the training set of increased number of projection images (for example, of N*2) can be downsampled (for example, to N projection images) and the training system can process each downsampled projection image one pixel at a time. The neighborhood of pixels used during training would be extended to include pixels from neighboring projection images along with the neighborhood of pixels from the individual projection image. This larger neighborhood can be transformed into a fixed length vector (e.g., length 18), which can be used as input to a NN interpolator. An output of the NN interpolator can be a fixed length vector (e.g., length 1 of real numbers) that can be transformed into an increased number of projection images (e.g., N*2).

Although embodiments of systems and methods are described herein generally with respect to a "2 by 2 binning mode," the application is not intended to be so limited. For example, embodiments of the application can be used to generate super-resolution binning modes for 2 by 1 binning, 1 by 2 binning, 4 by 4 binning, 5 by 3 binning or the like. In one embodiment, a limited number of or a single binning mode such as 2 by 2 binning can be supplemented/replaced by a corresponding super-resolution binning mode. Embodiments of the application can provide a super-resolution binning mode for each of a plurality of kVp settings and/or filtration settings (e.g., Al, Cu, specific thickness) for a corresponding examination. For example, when a wrist x-ray can be taken using 100 kVp, 110 kVp or a 120 kVp setting, a corresponding CBCT imaging system can use a NN interpolation 450 trained for each of the three settings of kVp. In one perspective, the NN interpolator can be considered to have a selectable setting (e.g., corresponding training) for each of a plurality of kVp settings for an examination type.

Although described herein with respect to CBCT digital radiography systems, embodiments of the application are not intended to be so limited. For example, other DR imaging system such as dental DR imaging systems, mobile DR imaging systems or room based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

DR detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

Cone beam CT for weight-bearing knee imaging as well as for other extremities is a promising imaging tool for diagnosis, preoperative planning and therapy assessment.

It should be noted that the present teachings are not intended to be limited in scope to the embodiments illustrated in the figures.

As used herein, controller/CPU for the detector panel (e.g., detector 24, FPD) or imaging system (controller 30 or detector controller) also includes an operating system (not shown) that is stored on the computer-accessible media RAM, ROM, and mass storage device, and is executed by processor. Examples of operating systems include Microsoft Windows®, Apple MacOS®, Linux®, UNIX®. Examples are not limited to any particular operating system, however, and the construction and use of such operating systems are well known within the art. Embodiments of controller/CPU for the detector (e.g., detector 24) or imaging system (controller 30) are not limited to any type of computer or computer-readable medium/computer-accessible medium (e.g., magnetic, electronic, optical). In varying embodiments, controller/CPU comprises a PC-compatible computer, a MacOS®-compatible computer, a Linux®-compatible computer, or a UNIX®-compatible computer. The construction and operation of such computers are well known within the art. The controller/CPU can be operated using at least one operating system to provide a graphical user interface (GUI) including a user-controllable pointer. The controller/CPU can have at least one web browser application program executing within at least one operating system, to permit users of the controller/CPU to access an intranet, extranet or Internet world-wide-web pages as addressed by Universal Resource Locator (URL) addresses. Examples of browser application programs include Safari® and Microsoft Internet Explorer®.

In addition, while a particular feature of an embodiment has been disclosed with respect to only one of several implementations or embodiments, such feature can be combined with one or more other features of the other implementations and/or other exemplary embodiments as can be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "exemplary" indicates the description is used as an example, rather than implying that it is an ideal.

The invention has been described in detail with particular reference to exemplary embodiments, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for digital radiographic 3D volume image reconstruction of a subject, executed at least in part on a computer, comprising:
    obtaining image data at a first binning mode for a plurality of 2D projection images over a range of scan angles;
    generating, for each of the plurality of 2D projection images, an increased-spatial resolution projection image by:
        (i) providing an image representation of a different corresponding object at a second higher spatial resolution binning mode;
        (ii) determining an image data transformation for the first binning mode according to the image representation obtained at the second higher spatial resolution binning mode;
        (iii) applying the image data transformation individually to the plurality of 2D projection images obtained at the first binning mode to generate the increased-spatial resolution plurality of 2D projection images; and
    storing the increased-spatial resolution plurality of 2D projection images in a computer-accessible memory.

2. The method of claim 1 wherein the transformed plurality of 2D projection images comprises a higher modulation transfer function (MTF) than the first binning mode or the transformed plurality of 2D projection images comprise a higher Nyquist frequency than the first binning mode.

3. The method of claim 1 further comprising processing the plurality of increased-spatial projection images to reconstruct the 3D volume image reconstruction of the subject.

4. The method of claim 3 wherein the 3D volume image reconstruction comprises a higher MTF than the first binning mode or the 3D volume image reconstruction comprises a higher Nyquist frequency than the first binning mode.

5. The method of claim 1 wherein providing an image representation of a different corresponding object at a second higher spatial resolution binning mode comprises selecting a first high resolution image of the corresponding object, and wherein determining an image data transformation for the first binning mode comprises:
    down-sampling the first high resolution image to the spatial resolution of the first binning mode;
    iteratively interpolating the down-sampled image to obtain a second estimated high resolution image of the corresponding object; and
    determining the image data transformation when an error between the first high resolution image and the second estimated high resolution image is less than a prescribed threshold.

6. The method of claim 1 wherein obtaining image data for a plurality of 2D projection images comprises obtaining image data from a cone-beam computerized tomography apparatus.

7. The method of claim 1 further comprising:
    processing the plurality of increased-spatial projection images to reconstruct a 3D volume image reconstruction of the subject;
    displaying the 3D volume image reconstruction; and
    storing the 3D volume image reconstruction in the computer-accessible memory, wherein the 3D volume image reconstruction is a orthopedic medical image, a dental medical image, a pediatric medical image or generated by image data from a flat panel detector.

8. The method of claim 7 wherein processing the plurality of increased-spatial projection images comprises:
    performing one or more of geometric correction, scatter correction, beam-hardening correction, and gain and offset correction on the plurality of 2D projection images;
    performing a logarithmic operation on the increased-spatial resolution plurality of 2D projection images to obtain line integral data; and
    performing a row-wise ramp linear filtering to the line integral data.

9. The method of claim 1 wherein the subject is a limb, an extremity, a weight bearing extremity or a portion of a dental arch.

10. The method of claim 1 wherein a plurality of image representations of the different corresponding object at the second higher spatial resolution binning mode are used to determine the image data transformation for the first binning mode for a single cone-beam computed tomography scan.

11. The method of claim 1 wherein the image data transformation is based on an examination type and x-ray radiation source exposure setting.

12. The method of claim 1 wherein the image data transformation is angularly independent.

13. The method of claim 1 wherein the image data transformation is provided by a neural network interpolator.

14. The method of claim 1 wherein the image data transformation is provided by a plurality of neural network interpolators.

15. A method for digital radiographic 3D volume image reconstruction of a subject, executed at least in part on a computer, comprising:
    obtaining cone-beam computed tomography image data at a first binning mode for a plurality of 2D projection images over a range of scan angles;

generating, for each of the plurality of 2D projection images, an increased-spatial resolution projection image by:
  (i) providing an image data transformation for the first binning mode according to image data from a second higher spatial resolution binning mode;
  (ii) applying the image data transformation individually to the plurality of 2D projection images obtained at the first binning mode to generate the increased-spatial resolution plurality of 2D projection images; and
storing the increased-spatial resolution plurality of 2D projection images in a computer-accessible memory.

16. A digital radiography CBCT imaging system for digital radiographic 3D volume image reconstruction of a subject, comprising:
  a DR detector to obtain a plurality of CBCT 2D projection images over a range of scan angles at a first binning mode;
  a computational unit to generate, for each of the plurality of 2D projection images, an increased-spatial resolution projection image, the computational unit to select (i) an image data transformation for the first binning mode according to image data from a second higher spatial resolution binning mode, and (ii) apply the image data transformation individually to the plurality of 2D projection images obtained at the first binning mode to generate the increased-spatial resolution plurality of 2D projection images; and
  a processor to store the increased-spatial resolution plurality of 2D projection images in a computer-readable memory.

17. The digital radiography CBCT imaging system of claim 16, where the computational unit is a neural network interpolator.

* * * * *

UNITED STATES PATENT AND TRADEMARK OFFICE
CERTIFICATE OF CORRECTION

PATENT NO. : 8,705,828 B2  
APPLICATION NO. : 13/222461  
DATED : April 22, 2014  
INVENTOR(S) : Dong Yang et al.

Page 1 of 1

It is certified that error appears in the above-identified patent and that said Letters Patent is hereby corrected as shown below:

In the Specification

Column 9, line 26    Please replace the word "tank" with the word --tanh--

Signed and Sealed this  
Thirteenth Day of January, 2015

Michelle K. Lee  
*Deputy Director of the United States Patent and Trademark Office*